United States Patent [19]

Bär et al.

[11] Patent Number: 4,602,622
[45] Date of Patent: Jul. 29, 1986

[54] MEDICAL EXAMINATION INSTALLATION

[75] Inventors: Ulrich Bär, Nuremberg; Walter Huk, Erlangen, both of Fed. Rep. of Germany

[73] Assignee: Siemens Aktiengesellschaft, Berlin & Munich, Fed. Rep. of Germany

[21] Appl. No.: 203,792

[22] Filed: Nov. 3, 1980

[30] Foreign Application Priority Data

Dec. 5, 1979 [DE] Fed. Rep. of Germany ....... 2948986

[51] Int. Cl.$^4$ .............................................. A61B 19/00
[52] U.S. Cl. .................................................. 128/303 B
[58] Field of Search ..................................... 128/303 B

[56] References Cited

U.S. PATENT DOCUMENTS 3,974,388  8/1976  Distler et al. .................... 250/445 T
4,058,114  11/1977  Soldner ........................... 128/303 B

FOREIGN PATENT DOCUMENTS 2139433  2/1973  Fed. Rep. of Germany ... 128/303 B

Primary Examiner—Michael H. Thaler
Attorney, Agent, or Firm—Hill, Van Santen, Steadman & Simpson

[57] ABSTRACT

In an exemplary embodiment, a computer tomography apparatus for producing transverse layer images has a patient-targeting device with a biopsy needle for being introduced into the patient along a path determined by the targeting device. A phantom apparatus with adjustable simulation parts for specific body locations provides for the alignment of the targeting device either via a simulation targeting device which is aligned using the simulation parts, or by releasably coupling the patient-targeting device (5) itself with the phantom apparatus for purposes of alignment.

5 Claims, 15 Drawing Figures

MEDICAL EXAMINATION INSTALLATION

BACKGROUND OF THE INVENTION

In modern x-ray diagnostics, computer tomographs are increasingly employed in which the patient is scanned in a transverse layer by means of a measuring arrangement comprised of an x-ray source and a radiation receiver. From the measured values, delivered by the radiation receiver, which measured values correspond to the attenuation of the x-radiation in the patient, a computer calculates an image of the scanned transverse layer. An important field of application of a computer tomograph is the examination of the cranium; for example, for the detection of tumors. If a tumor is ascertained in the x-ray image, it is necessary to remove a tissue specimen from the tumor tissue. The problem which arises here is to guide a biopsy needle in a directed fashion through a bone gap in the skull in such a fashion that said needle precisely reaches the location of the tissue at which a tissue specimen is to be removed.

SUMMARY OF THE INVENTION

The object underlying the invention resides in producing a medical examination installation which permits examinations to be conducted with the aid of a computer tomograph and tissue specimens to be removed in a targeted fashion on the basis of the computer tomography images.

In accordance with the invention, this object is achieved in that the medical examination installation comprises a computer tomograph for transverse layer images with patient positioning means, a patient targeting device with means for introduction into the patient which are capable of alignment (or orientation) by means of the targeting device, and a phantom apparatus with adjustable simulation parts for specific body locations, a simulation-targeting device, capable of alignment (or orientation) to the simulation parts, or means for connection of the patient targeting device with the phantom apparatus. In the case of the inventive examination installation, the patient can be secured in a non-dislocatable fashion into the positioning means. With the aid of the patient targeting device and a computer tomography image, an adjustment of the phantom apparatus corresponding to the existing conditions is possible. The simulation targeting device can then be aligned (or orientated) to a specific body location and its alignment can be transmitted to the patient targeting device. However, it is also possible to align the patient targeting device on the phantom apparatus, to remove it from this apparatus and to connect it with the positioning means for the patient, so that only a single targeting device is necessary.

An embodiment of the invention has the feature that every targeting device exhibits a support-mounting for a biopsy needle which permits a free adjustment of the biopsy needle in space. In this embodiment, the removal of tissue specimens, for example from a tumorous tissue, is possible with the aid of a biopsy needle. It is furthermore advantageous to provide every simulation part with a mark which is adjustable in a plane of a wheel, and to adjustably mount the wheel for displacement in the direction of its axis. Thus, for example, two wheels can be provided on the phantom apparatus; one in order to simulate the bone gap in the skull of a patient for the purpose of introducing a biopsy needle, and the other in order to simulate the plane in which a tissue specimen is to be removed.

The invention shall be explained in greater detail in the following on the basis of an exemplary embodiment illustrated on the accompanying drawing sheets; and other objects, features and advantages will be apparent from this detailed disclosure and from the appended claims.

DETAILED DESCRIPTION

Figure 1:
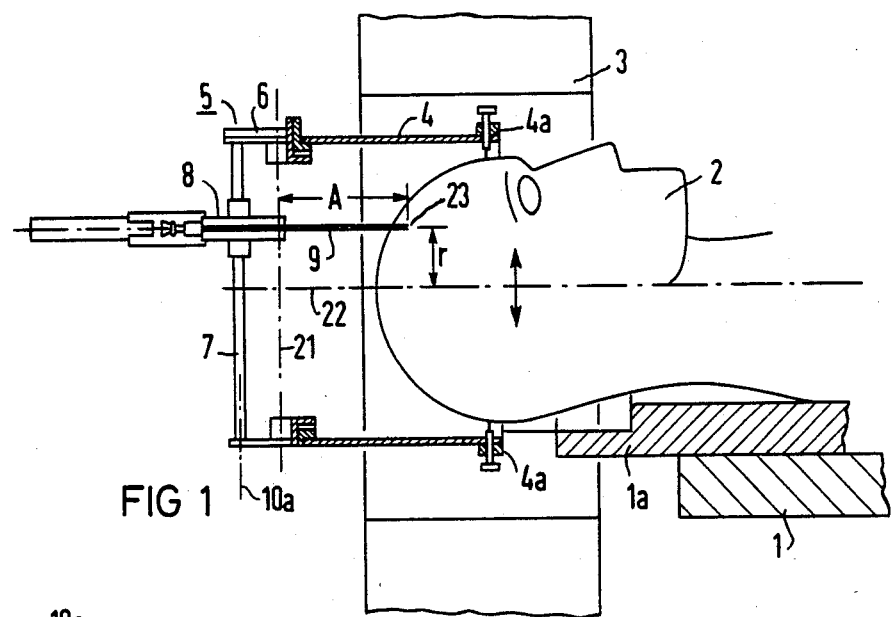
FIG. 1 illustrates a computer tomograph with positioning means and a patient targeting device of an examination installation in accordance with the invention.
Figure 2:
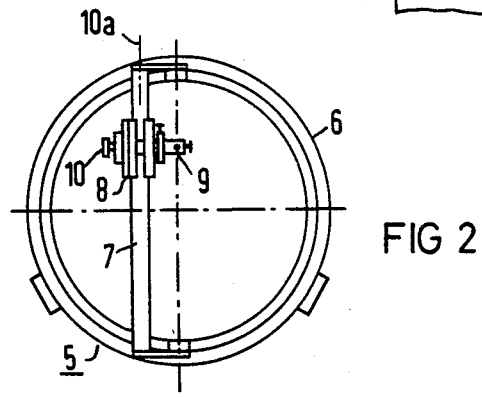
FIG. 2 illustrates a view of the targeting device according to FIG. 1.
Figure 3:
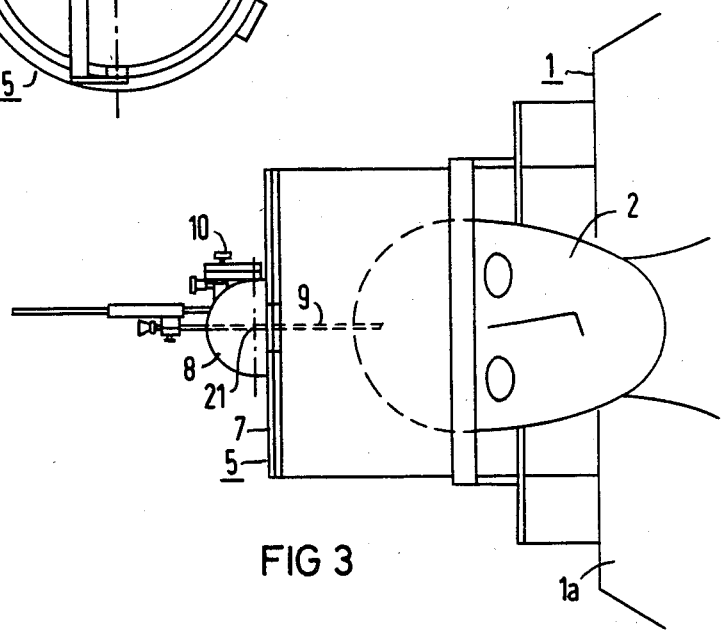
FIG. 3 illustrates the targeting device according to FIGS. 1 and 2 from above.
Figure 4:
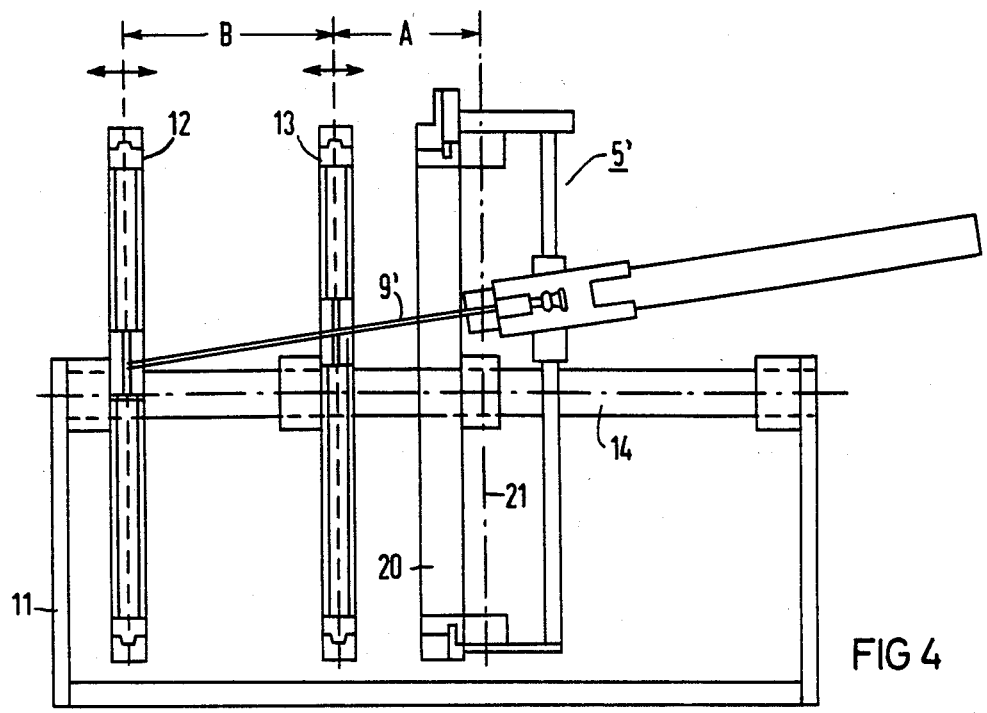
FIG. 4 illustrates a phantom apparatus of an examination installation in accordance with the invention.

In FIGS. 1 and 3 a patient support 1 is illustrated on which a support plate 1a with a patient 2 rests. The head of the patient 2 is fixed (or positioned) in the opening of a schematically illustrated computer tomograph 3 with the aid of positioning means 4. The positioning means 4 is provided with screw threaded elements arranged in a ring 4a, which abut against the head of the patient 2 and hold the latter securely in position. The ring 4a with a patient targeting device 5 is adjustable in height relative to the support plate 1a. The patient targeting device 5 is connected with the positioning means 4 and, according to FIG. 2, exhibits, on an annular frame 6, a yoke (or cross bar) 7 which bears, in a longitudinally-displaceable fashion, a holder 8 for a biopsy needle 9. The biopsy needle 9 is mounted by the holder 8 for pivotal movement about two axes 10, 10a (FIG. 2), which are perpendicular to one another, and is therefore freely adjustable in space. The holder 8 may be fixed at a desired position in space by means of set screws such as indicated at 10.

The phantom apparatus according to FIGS. 4 through 7 exhibits, on a base 11, simulation parts for specific body locations which are formed by wheels 12, 13. The wheels 12, 13 are mounted on a shaft 14. The wheel 12 bears (or supports), according to FIG. 5, a mark 16 which is longitudinally displaceable on a spoke 15; i.e., which is adjustable in the plane of wheel 12 along the length of a diameter. Analogously to this, wheel 13 bears a mark 18, FIG. 6, which is adjustable on a spoke 17 along the length of a diameter. The mark 18 is formed by a hole (or aperture) in a plate 19. On the shaft 14 a holder 20 is mounted which bears a targeting device 5' which corresponds to the targeting device 5 of FIGS. 1 through 3.

Figure 8:
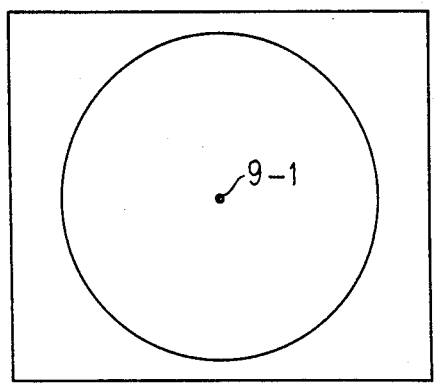
FIGS. 8 through 12 illustrate tomographic images for the purpose of explaining the adjustment of the targeting device.

For the removal of a tissue specimen by means of the biopsy needle 9, which is freely adjustable on the targeting device 5, one proceeds in the following fashion:

The biopsy needle 9 of the targeting device 5 is positioned in its zero-position in which it lies along the center axis 22 of the targeting device 5. Subsequently, by means of the computer tomograph 3, which, for example, can be designed in accordance with the German No. OS 2,438,708, a photographic exposure of the biopsy needle 9 is prepared which is illustrated in FIG. 8. The biopsy needle, in this photographic exposure, marks the reference center 9-1 which is of significance in terms of further evaluation (or analysis). After this photographic exposure, the apparatus can no longer be permitted to be displaced.

First the dimension A, FIG. 1, the distance between the reference plane 21 of the targeting device 5 and the bone gap 23 in the skull of the patient 2, is ascertained with the use of the targeting device 5. The dimension A is adjusted on the phantom apparatus according to FIG. 4 through axial displacement of the wheel 13 on shaft 14.

Figure 9:
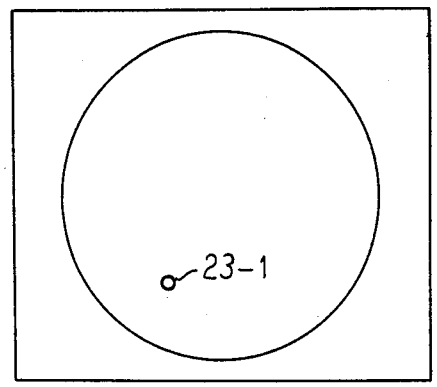

Subsequently, a photographic exposure of the bone gap 23 in the head of the patient 2 is prepared with the computer tomograph 3. This photographic exposure is illustrated in FIG. 9. It shows the transverse layer of the head of the patient 2 in which the bone gap 23 lies and shows the location of the bone gap at 23-1.

Figure 6:
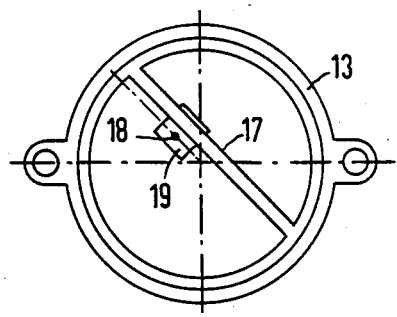
FIGS. 5 through 7 illustrate details of the phantom apparatus according to FIG. 4.
Figure 5:
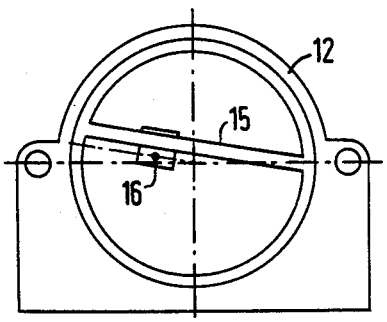
Figure 7:
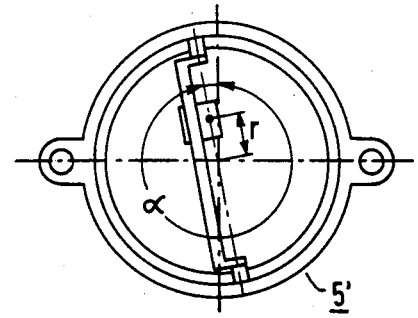
Figure 10:
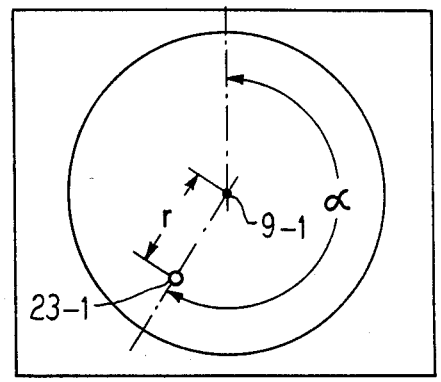

The images according to FIGS. 8 and 9 are superimposed and result in an image according to FIG. 10. From the image according to FIG. 10, the angle α and the distance r are ascertained and these values are adjusted on the wheel 13 with the aid of the mark 18 (FIG. 6).

Figure 11:
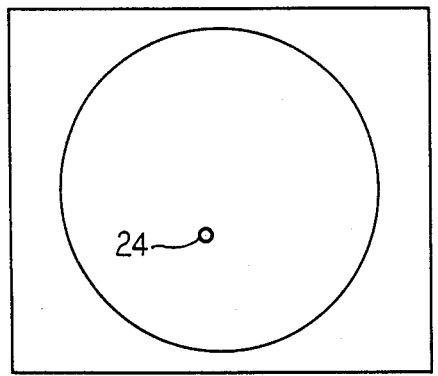

By means of the computer tomograph apparatus 3, an image is now formed of that particular transverse layer in which the target point, for example a tumor, lies. One obtains an image such as shown in FIG. 11. In the case of this photographic exposure, the value B, namely the distance between the transverse layer in which the bone gap 23 is disposed, and the transverse layer in which the target point is disposed, must be read off and adjusted in the phantom apparatus according to FIG. 4 through axial displacement of the wheel 12.

Figure 12:
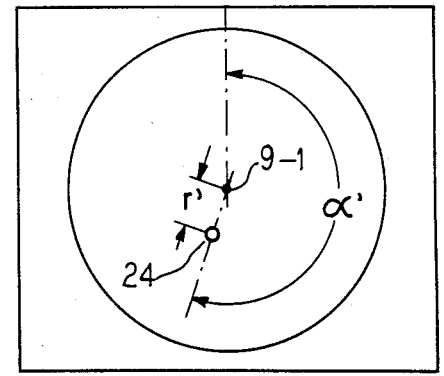

If the images according to FIGS. 8 and 11 are superimposed, then the image according to FIG. 12 is obtained, with imaged points 9-1 and 24. From this image, the angle α' and the distance r' are ascertained and the mark 16 of the wheel 12 (FIG. 5) is adjusted corresponding to these values.

The biopsy needle 9' of the phantom apparatus is now so adjusted that it runs through the mark 18 of the wheel 13 and points to (or aims at) the mark 16 of the wheel 12.

Two possibilities now arise. In case the targeting devices 5, 5' are two separate targeting devices, the values adjusted at the targeting device 5' are transferred to the targeting device 5. Following this transfer, the biopsy needle 9 has the correct position and its tip is disposed at the location at which tissue is to be removed. The second possibility is to provide only a single targeting device and to remove this targeting device from the phantom apparatus subsequent to adjustment and to connect it with the positioning device 4. Naturally, the values adjusted on the phantom apparatus must here be fixed as by tightening of set screws or the like prior to the transfer.

Figure 13:
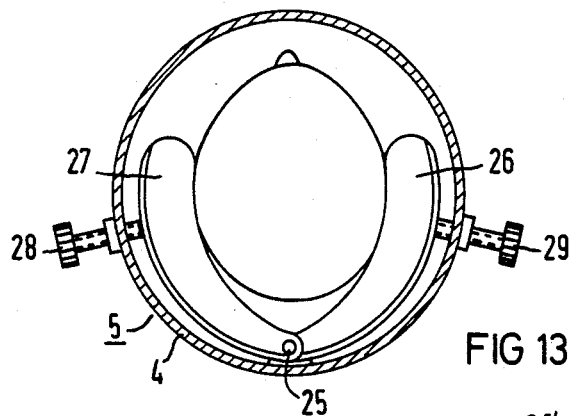
FIGS. 13 through 15 illustrate variants of the positioning means which are particularly expedient.
Figure 14:
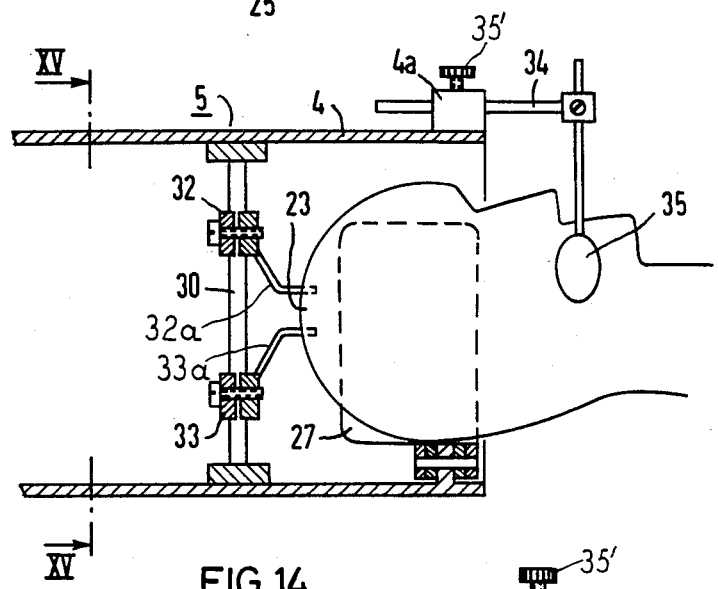
Figure 15:
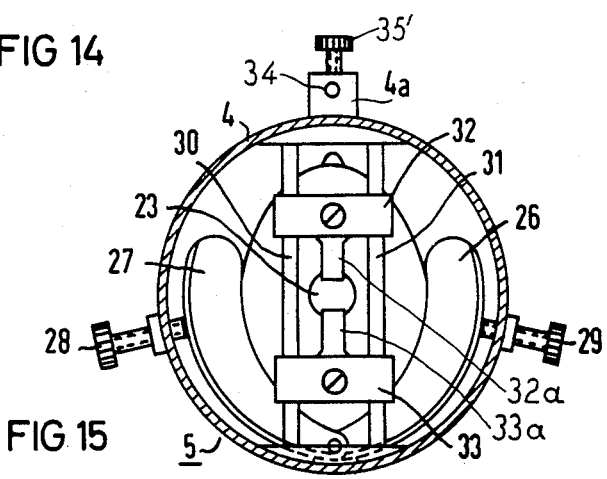

The positioning means illustrated in FIGS. 13 through 15 exhibit two bolsters (or cushions) 26, 27, which are interconnected in an articulated fashion by means of a hinge joint 25. The bolsters 26, 27 are mounted on rigid base plates and can be pressed against the head of the patient by means of adjustment screws 28, 29. For the purpose of further positioning, two clamps 32, 33, which are longitudinally displaceable and arrestable (or lockable) on guides 30, 31 (FIG. 15) are provided which have extensions 32a, 33a introduced into the bone gap 23 and braced therein. In addition, a bolster 35 (FIG. 14) is mounted on a holder 34, which bolster is introduced into the mouth of the patient and fixed in position in the upper jaw bone (or superior maxilla). The holder 34 can be displaced relative to a mounting block 4a and arrested (or locked) in an adjusted position by means of a set screw 35'.

It will be apparent that many modifications and variations may be effected without departing from the scope of the novel concepts and teachings of the present invention.

We claim as our invention:

1. A medical examination system, comprising a computer tomography apparatus (1, 3) for producing transverse layer images; positioning means (4) for positioning a patient (2) relative to said apparatus (1, 3); a patient-targeting device (5) for operative association with said positioning means (4) and adjustable to define a desired path orientation relative to a patient positioned by said positioning means for the introduction of an instrument (9) into the patient (2); and a phantom apparatus (FIG. 4) comprising adjustable simulation parts (12, 13, 15 through 19) for simulating a path in a specified body location, and providing for orientation of the targeting device by means of the adjustment of the simulation parts (12, 13, 15 through 19) with the use of patient transverse layer images produced by said computer tomography apparatus (1, 3), said simulation parts having mechanically adjustable marking means mounted thereon for physical adjustment in space to respective locations in respective layer simulating planes corresponding to respective locations in the patient transverse layer images, thereby to define the desired path in space.

2. A medical examination system according to claim 1, characterized in that said targeting device (5, 5') exhibits a support-mounting (6, 7, 8) for a biopsy needle (9, 9') which permits a free adjustment of the biopsy needle (9, 9') in space.

3. A medical examination system according to claim 1, characterized in that each simulation part (12, 13, 15 through 19) comprises a wheel (12, 13), and a mark (16, 18), adjustable in the plane of the wheel (12, 13), and the wheel (12, 13) being adjustably mounted in the direction of its axis.

4. A medical examination system according to claim 1, with said phantom apparatus further comprising a simulation targeting device (5') with a simulation instrument (9') and adjustable correspondingly to said patient-targeting device such that the orientation of the simulation instrument (9') in the simulation targeting device (5') by means of the adjustment of the simulation parts (12, 13, 15 through 19) is directly transferable so as to provide for corresponding orientation of the patient targeting device (5) to define a desired path orientation for the introduction of the instrument (9).

5. A medical examination system according to claim 1, with said phantom apparatus having means (20, 9') for releasably coupling said patient targeting device (5) in predetermined operative association with said adjustable simulation parts (12, 13, 15 thorugh 19) such that adjustment of said simulation parts directly actuates said patient targeting device to a corresponding orientation while the patient targeting device is coupled with said simulation parts.

* * * * *